US006710025B1

(12) United States Patent
Spector

(10) Patent No.: US 6,710,025 B1
(45) Date of Patent: Mar. 23, 2004

(54) TREATMENT OF DAMAGED TISSUE USING AGENTS THAT MODULATE THE ACTIVITY OF ALPHA-SMOOTH MUSCLE ACTIN

(75) Inventor: Myron Spector, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 09/576,180

(22) Filed: May 23, 2000

Related U.S. Application Data

(60) Provisional application No. 60/136,235, filed on May 26, 1999.

(51) Int. Cl.$^7$ .................. A61K 38/00; A61K 38/21; C12N 5/08; C07K 17/00

(52) U.S. Cl. ................ 514/2; 514/12; 424/85.4; 424/85.5; 435/360; 435/375; 530/351; 530/399

(58) Field of Search ............... 514/2, 12, 21; 424/85.1, 85.4, 85.5, 548, 572; 530/351, 399; 435/360, 375

(56) References Cited

U.S. PATENT DOCUMENTS

| 5,428,010 A | 6/1995 | Murray et al. ............. 514/12 |
| 5,656,587 A | 8/1997 | Sporn et al. ............. 514/2 |
| 5,741,777 A | 4/1998 | Grinnell et al. ............ 514/12 |
| 5,902,741 A | 5/1999 | Purchio et al. ........ 435/240.23 |

FOREIGN PATENT DOCUMENTS

| EP | 0 952 792 B1 | 8/2003 | ............. A61F/2/02 |
| JP | 501706 | 2/1998 | ........... A61L/27/00 |
| JP | 505250 | 5/1998 | ............ A61F/2/08 |
| WO | WO 95/26761 | 10/1995 | ........... A61L/27/00 |
| WO | WO 95/28950 | 11/1995 | .......... A61K/38/18 |
| WO | WO 95/33421 | 12/1995 | ............ A61F/2/02 |
| WO | WO 96/40175 | 12/1996 | .......... A61K/35/14 |
| WO | WO 97/07136 | 2/1997 | .......... C07K/16/24 |
| WO | WO 97/41886 | 11/1997 | .......... A61K/38/21 |

OTHER PUBLICATIONS

Desmoulere et al. alpha–Smooth Muscle Actin is Expressed in a Subpopulation of Cultured and Cloned Fibroblasts and is Modulated by gamma–Interferon. (1992) Experimental Cell Research, vol. 201, pp64–73.*

çomut, et al., "Association of Fibroblast Orientation Around Titanium in Vitro with Expression of a Muscle Actin," *Biomaterials* 21:1887–1896 (2000).

Dennison, et al., "Differential Effect of TGF–β–1 and PDGF on Proliferation of Periodontal Ligament Cells and Gingival Fibroblasts," *Growth Factors and Fibroblasts of the Periodontium* 65:641–648 (1994).

DesRosiers, et al., "Proliferative and Matrix Synthesis Response of Canine Anterior Cruciate Ligament Fibroblasts Submitted to Combined Growth Factors," *J. Ortho. Res.* 14:200–208 (1996).

Lind, "Principles for Enhancement of Bone Healing and Bone Formation," *Acta. Orthop. Scand. Supp.* 283:2–37 (1998).

Masur, et al., "Myofibroblasts Differentiate from Fibroblasts When Plated at Low Density," *Proc. Natl. Acad. Sci. USA* 93:4219–4223 (1996).

Menard, et al., "Contractile Behavior of Smooth Muscle Actin–Containing Osteoblasts in Collagen–GAG Matrices in Vitro: Implant–Related Cell Contraction," *Biomaterials* 21:1867–1877 (2000).

Mueller, et al., "α–Smooth Muscle Actin nd Contractile Behavior of Bovine Meniscus Cells Seeded in Type I and Type II Collagen–GAG Matrices," *J. Biomed. Materials Res.* 45:157–166 (1999).

Mueller, et al., "Meniscus Cells Seeded in Type I and Type II Collagen–GAG Matrices in Vitro," *Biomaterials* 20:701–709 (1999).

Murray, et al., "Fibroblast Distribution in the Anteromedial Bundle of the Human Anterior Cruciate Ligament: The Presence of α–Smooth Muscle Actin–Positive Cells," *J. Ortho. Res.* 17:18–27 (1999).

Schneider, et al., "Expression of α–Smooth Muscle Actin in Canine Intervertebral Disc Cells in Situ and in Collagen–Glycosaminoglycan Matrices in Vitro," *J. Ortho. Res.* 17:192–199 (1999).

Schulz Torres, et al., "Tendon Cell Contraction of Collagen–GAG Matrices in Vitro: Effect of Cross–Linking," *Biomaterials* 21:1607–1619 (2000).

Woo, et al., "Engineering the Healing of the Rabbit Medial Collateral Ligament," *Med. Biol. Eng. Comput.* 36:359–364 (1998).

Yokozeki, et al., "Interferon–γ Inhibits the Myofibroblastic Phenotype of Rat Palatal Fibroblasts Induced by Transforming Growth Factor–β1 in Vitro," *FEBS Letters* 442:61–64 (1999).

Arnoczky, et al., "Meniscal Repair Using an Exogenous Fibrin Clot," *J. Bone Joint Surg.* 70–A:1209–1217 (1988).

Arnoczky, et al., "Meniscal Replacement Using a Cryopreserved Allograft," *Clin. Orthop. Rel. Res.*:252–121–128 (1990).

Darby, et al., "α–Smooth Muscle Actin Is Transiently Expressed by Myofibroblasts During Experimental Wound Healing," *Lab. Invest.* 63:21–29 (1990).

Eddy, et al., "Evidence for the Nonmuscle Nature of the 'Myofibroblast' of Granulation Tissue and Hypertropic Scar," *Am. J. Pathol.* 130:252–260 (1988).

Herman, "Actin Isoforms," *Curr. Opin. Cell Biol.* 5:48–55 (1993).

(List continued on next page.)

Primary Examiner—Gary Kunz
Assistant Examiner—Jegatheesan Seharaseyon
(74) Attorney, Agent, or Firm—Michael A. Sanzo; Fitch, Even, Tabin & Flannery

(57) ABSTRACT

The present invention is directed to therapeutic methods that are based upon an ability to modulate cellular contraction. This is accomplished by administering agents that either inhibit or induce the activity of alpha-smooth muscle actin.

19 Claims, No Drawings

OTHER PUBLICATIONS

Jester, et al., "Expression of α–Smooth Muscle (α–SM) Actin During Corneal Stromal Wound Healing," *Invest. Ophthal. Vis. Sci. 36*:809–819 (1995).

Klompmaker, et al., "Porous Polymer Implant for Repair of Meniscal Lesions: A Preliminary Study in Dogs," *Biomaterials 12*:810–816 (1991).

Milachowski, et al., "Homologous Meniscus Transplantation," *Intl. Orthop. 13*:1–11 (1989).

Nehrer, et al., "Matrix Collagen Type and Pore Size Influence Behavior of Seeded Canine Chondrocytes," *Biomaterials 18*:769–776 (1997).

Saga, et al., "Phenotype–Dependent Expression of α–Smooth Muscle Actin in Visceral Smooth Muscle Cells," *Exp. Cell Res. 247*:279–292 (1999).

Siegel, et al., "Meniscal Allografts," *Clin. Sports Med. 12*:59–80 (1993).

Stone, et al., "Regeneration of Meniscal Cartilage with Use of a Collagen Scaffold," *J. Bone Joint. Surg. 79–A*:1770–1777 (1997).

Stone, et al., "Future Directions," *Clin. Orthop. Res. 252*:129–135 (1990).

Stone, et al., "Meniscal Regeneration with Copolymeric Collagen Scaffolds," *Am. J. Sports Med. 20*:104–111 (1992).

Toyonaga, et al., "Substitute Meniscus of Teflon–net for the Knee Joint of Dogs," *Clin. Orthop Res. 179*:291–297 (1983).

Welch, et al., "Temporal Relationships of F–Actin Bundle Formation, Collagen and Fibronectin Matrix Assembly, and Fibronectin Receptor Expression to Wound Contraction," *J. Cell Biol. 110*:133–145 (1990).

Zhang, et al., "Lung Fibroblast α–Smooth Muscle Actin Expression and Contractile Phenotype in Bleomycin–Induced Pulmonary Fibrosis," *Am. J. Pathol. 148*:527–537 (1996).

\* cited by examiner

TREATMENT OF DAMAGED TISSUE USING AGENTS THAT MODULATE THE ACTIVITY OF ALPHA-SMOOTH MUSCLE ACTIN

CROSS-REFERENCE TO RELATED APPLICATIONS

The present application claims priority under 35 U.S.C. §119(e) to U.S. provisional application No. 60/136,235, filed on May 26, 1999.

FIELD OF THE INVENTION

The present invention is directed to methods for controlling cellular contraction and to medical treatments that rely upon this control. The methods are important in the treatment of ligament damage, osteoporosis, wound healing, tissue engineering, drug delivery, and the prevention of tumor cell metastasis.

BACKGROUND OF THE INVENTION

Cellular contraction plays a role in a number of biological activities that have therapeutic consequences. The contraction of fibroblasts, grown on a matrix in vitro as part of a tissue engineering protocol for replacing a damaged ligament, may alter the size, shape, and porosity of the matrix and thereby jeopardize the performance of the implant. In vivo, inappropriate contraction may make the reattachment of the ends of a ruptured ligament to each other or to bone difficult or limit the movement of limbs as a result of excessive contracture. This scenario also applies to other musculoskeletal tissue cells and to epithelial cells such as endothelial cells and liver.

Cellular contraction also plays an important role in wound healing. Although contraction may initially promote healing, it can also lead to significant scarring and a loss of physiological function (see U.S. Pat. No. 5,741,777). The adverse effects of contraction are particularly severe in surgical and burn patients. In addition, scarring may cause secondary damage to patients that have incurred damage to the spinal cord or other severe trauma.

Other biological activities believed to depend, in part, on cellular contraction include osteoporosis (where the contraction of osteoblasts results in their retraction, thus allowing bone resorption to proceed) and in tumor cell metastasis. In the latter case, cancer cells must typically pass an endothelial cell barrier before they can enter into the bloodstream and be carried to a distant site for colonization. Agents that prevent endothelial cells from contracting (and thereby retracting) should therefore make metastasis more difficult. addition to its importance in ligament repair, tissue engineering, wound healing, osteoporosis and metastasis, the ability to control cell contraction may lead to improved procedures for drug delivery. For example, an agent that promoted endothelial cell contraction might be include in intranasal or intramuscular vehicles to aid in the passage of drug through the walls of capillaries. Such agents may also aid substances already in the bloodstream in exiting into tissue.

Alpha smooth muscle actin (SMA) is a particular isoform of actin that may cause the contraction of vascular smooth muscle cells (Saga, et al., *Exp. Cell Res.* 249:279–292 (1999)). It is known to be expressed in myofibroblasts during wound healing and in tissues undergoing fibrosis (Zhang, et al., *Am. J. Pathol.* 148:527–537(1996) Jester, et al., *Opthal. Vis. Sci.* 36:809–819(1995); Darby, et al., *Lab. Invest.* 63:21–28 (1990)). The complete nucleotide and amino acid sequences of the human form of the gene have been reported (Herrman, *Curr. Opin. Cell Biol.* 5:48–55 (1993)).

SUMMARY OF THE INVENTION

The present invention is based upon the discovery that SMA is responsible for the contraction of a variety of cells other than fibroblasts and for which such activity was not previously known. Agents that inhibit SMA activity prevent these cells from contracting, whereas agents that induce SMA activity promote contraction. Examples of SMA inhibitors include platelet derived growth factor (PDGF), staurosporin and interferons. An example of an SMA inducer is transforming growth factor-β (TGF-β).

In its first aspect, the present invention is directed to methods of repairing musculoskeletal tissue (including bone, articular cartilage, meniscus, tendon intervertebral disk and especially damaged ligaments) and epithelial tissue. One procedure for accomplishing this involves removing cells from a patient's body, growing them on a matrix, and then implanting the matrix/cell combination at the site of the damage, e.g. at the site of a torn ligament. This approach has been referred to as "tissue engineering." The cells used may be any of the musculoskeletal, or epithelial cells mentioned above. Alternatively, marrow stromal stem cells may be used and have the advantage of being relatively easy to obtain. Matrices may be made out of several different types of biologically compatible material, but type I collagen and synthetic polymers, such as polylactic acid and polyglycolic acid, will typically be employed. The invention is directed to an improvement in this procedure in which cells grown on matrices in vitro are treated with a concentration of an agent sufficient to either inhibit or promote the expression or biological action of alpha-smooth muscle actin (SMA). Among the agents that maybe used for inhibiting contraction are PDGF and interferon. The activity of SMA may also be reduced by preventing its expression using an antisense oligonucleotide, particularly an oligonucleotide complementary to the promoter region of the human SMA gene. Among the agents that may be used to promote contraction is TGF-β.

The invention is also directed to a method of treating a patient for damaged musculoskeletal tissue (particularly a damaged ligament), or epithelial tissue by sequentially administering, at the site of injury, an SMA inhibitor followed by an SMA inducer. The inhibitor should be given at a dosage and for a duration sufficient to promote tissue attachment. The time necessary for attachment to occur will vary from patient to patient, but will typically be between 1 and 10 weeks. The extent to which attachment has occurred may be determined by clinical examination and by diagnostic imaging techniques well known in the art. After attachment, the inducer should be administered for the purpose of causing the tissue to contract and thereby assume a more natural conformation. One example of a treatment protocol using this procedure would involve injections of TGF-beta at a concentration of between 100 ng/ml and 500 ug/ml at the site of ligament damage, e.g., the knee. After a period of, for example, 4 weeks, injections are made using a comparable concentration of PDGF or an interferon until healing is complete.

In another aspect, the invention is directed to a procedure for promoting the healing of wounded musculoskeletal tissue in a patient. Initially, an SMA inducer (TGF-beta, 100 ng/ml–500 ug/ml) is injected at the site of tissue damage at a dosage and for a duration sufficient to promote the closure of the wound. Once closure has been essentially completed, an SMA inhibitor (e.g., PDGF or an interferon in the concentration ranges recited above) may be administered at the site of the wound to reduce scar formation. In most cases, it is expected that administration will be accomplished using local delivery.

Inducers of SMA may also be administered to a patient for the purpose of enhancing drug absorption. A sufficient dosage should be given to induce endothelial cell contraction. For example, TGF-β at a concentration of 100 ng/ml–500 ug/ml can be co-administered with a second drug either parenterally or intranasally.

The invention is also directed to a method of preventing tumor cell metastasis in a cancer patient. This may be accomplished by administering an agent that inhibits SMA in the endothelial cells of the vasculature. Because the endothelial cells do not contract, cancer cells shed from a main tumor mass is prevented from entering into the patient's bloodstream and those in the bloodstream are prevented from invading tissue.

DETAILED DESCRIPTION OF THE INVENTION

Treatment Methods

The ability to control the contraction of cells has important consequences with respect to at least six different therapeutic applications. First, it is important with respect to ligament repair procedures involving in vitro tissue engineering methods. Scientific articles describing such procedures include: Arnoczky, et al., *J. Bone Joint Surg.* 70A:1209–1217 (1988); Milachowski, et. Al., *Int. Orthop.* 13:1–11 (1989); Arnoczky, et al., Clin. Orthop. 252:121–128 (1990), Siegel, et al., *Clin. Sports Med.* 12:59–80 (1993); Stone, et al., *Am. J. Sports Med.* 20:104–111 (1992), Toyonaga, et al., *Clin. Orthop.* 179:291–297 (1983), Klompmaker, et al., *Biomaterials* 12:810–816(1991); Stone, et al., *J. Bone Joint Surg.* 79A: 1770–1777 (1997); Stone, et al., *Clin. Orthop.* 252:129–135(1990); Nehrer, et al., *Biomaterials* 18768–776(1997). Replacement ligaments may be prepared by removing cells from a patient's body and growing them on matrices containing collagen and similar materials. The contraction of the cells in vitro creates matrix distortions that complicate this procedure. It has now been discovered that agents modulating the activity of alpha-smooth muscle actin can be used to control cell contraction. The invention is compatible with any method of growing cells in vitro and involves simply adding an inhibitory agent to growth medium and/or to the matrix prior to the seeding of cells. For example, PDGF may be added to DMEM culture medium used for the growth of fibroblasts on a collagen/glycosaminoglycan matrix. The concentration of PDGF should generally be between 1 and 500 ng/ml and preferably between 10 and 50 ng/ml. This therapeutic approach to the treatment of ligament injuries also applies in the same way to injuries in bone, articular cartilage, meniscus, tendon, intervertebral disk, and for liver or other epithelial tissue engineering.

In vivo, inappropriate cellular contraction may make it difficult for natural or implanted ligaments to attach to bone properly and may restrict movement after attachment has been accomplished. In order to avoid these problems, an SMA inhibitor (e.g., a pharmaceutical preparation of PDGF at a concentration of between 100 ng/ml and 500 ug/ml) may be injected directly at the site of ligament damage to promote attachment. Administration should be repeated on a regular basis, e.g., twice a week, until standard clinical procedures and imaging techniques indicate that attachment is complete. An inducer of SMA may then be injected at the site of injury to cause the ligament to contract and thereby assume a more normal conformation. For example, TGF-β may be injected at a concentration of between 100 ng/ml and 500 ug/ml. As with the injections of the SMA inhibitor, the injections of inducer should be performed on a regular basis with results followed by periodic clinical evaluation. As with the in vitro methods discussed above, the in vivo procedures used for damaged ligaments can be applied in exactly the same way to the repair of bone, articular cartilage, meniscus, tendon and intervertebral disk.

Cellular contraction also plays an important role in wound repair (see, e.g., Mast, in *Wound Healing: Biochemical and Clinical Aspects*, Cohen et al., ed., WB Saunders Co. (1992)). Myofibroblasts expressing alpha-smooth muscle actin pull together the open margins of skin wounds to promote healing (Eddy et al., *Am. J. Pathol.* 130:252–260 (1988); Welch et al., *J. Cell. Biol.* 110:133–145 (1990)). In order to further promote contraction, an inducer of SMA maybe administered at the wound site. For example, TGF-beta may be administered in a topical preparation at a concentration of between 100 ng/ml and 500 ug/ml. The preparation should be changed periodically over a period of days until wound closure has been accomplished. To reduce scaring, a preparation containing one or more inhibitors of alpha-smooth muscle actin should then be administered either topically or by local injection. For example, a preparation containing PDGF at a concentration of between 100 ng/ml and 500 ug/ml may be injected. Injections should be repeated periodically until healing has been completed.

The expression and activity of alpha-smooth muscle actin in endothelial cells may be used to enhance drug delivery. Specifically, inducers of SMA may be used to promote the contraction of endothelial cells, thereby making it easier for drug to be absorbed into the vasculature of a patient. Thus, an agent such as TGF-β may be combined with a drug injected intramuscularly to aid in its absorption. Alternatively, an SMA inducer may be included in intranasal drug compositions to promote the absorption of therapeutic agents into the capillaries of the lung. In the case of TGF-β, it is expected that a concentration in the range of 100 ng/ml–500 ug/ml would be used in preparations.

Agents that inhibit endothelial cell contraction (e.g. PDGF) will make both the entry and exit of cells from a patient's bloodstream more difficult. Since one of the major events that must take place for tumor cell metastasis to occur is for cells to pass into and out of blood vessels, SMA inhibitors may be used as a treatment for patients with solid tumors. An inhibitor may be injected either systemically or it may be administered directly at the site of tumor occurrence. Topical preparations of inhibitor may also prove useful in certain instances, e.g. in the treatment of various types of skin cancer.

Agents inhibiting alpha-smooth muscle actin may also be used as a therapy for patients with osteoporosis. Systemic injections of agents such as PDGF or an interferon may be used to inhibit osteoblast retraction and thereby block osteoclast access to the bone surface for the purpose of calcium resorption. It is expected that this treatment will be used in conjunction with other established methods of treating osteoporosis involving the administration of agents such as calcium, vitamin D and parathyroid hormone. When PDGF or interferon is used as the inhibitor, it is expected that they will typically be injected in a pharmaceutical composition in a concentration range of between 100 ng/ml and 500 ug/ml.

Sustained release preparations are also appropriate for the treatment of osteoporosis patients and may be more convenient for patients than repeated parenteral administration.

Dosage

The total dosage of alpha-smooth muscle inhibitor or inducer administered to a patient will be determined based upon the particular condition being treated, the route of administration and the treatment of objective. A typical daily dose of inhibitor or inducer administered to a patient will, depending upon the agent used, be between 1 ug and 10 mg. Topical, intranasal and locally injected preparations will, typically, also fall within this range. These dosages are simply guidelines and the actual dosage selected for an individual patient will be determined by the attending physician based upon clinical conditions and using methods well known in the art. Agents may be provided in either a single or multiple dosage regimen and may be given either alone or in conjunction with other therapeutic agents.

Dosage Forms and Route of Administration

The present invention is compatible with any route of administration and any dosage form. Depending upon the particular condition being treated, certain dosage forms will tend to be more convenient or more effective than others. For example, local injection will be the preferred route of administration for accomplishing in vivo ligament repair whereas topical administration will generally be preferred in treating skin cancers. Apart from parenteral and topical preparations, agents may be administered orally, perorally, internally, intra nasally, rectally, vaginally, lingually, and transdermally. Specific dosage forms include tablets, pills, capsules, powders, aerosols, suppositories, skin patches, parenterals and oral liquids including suspensions, solutions and emulsions. Sustained release dosage forms may also be used. All dosage forms may be prepared using methods that are standard in the art (see e.g., *Remington's Pharmaceutical Sciences*, 16th, Ed. A. Oslo Editor, Easton, Pa. (1980).

Inhibitors and inducers of alpha-smooth muscle actin may be used in conjunction with any of the vehicles and excipients commonly employed in pharmaceutical preparations, e.g., talc, gum arabic, lactose, starch, magnesium sterate, cocoa butter, aqueous or non-aqueous solvents, oils, paraffin derivatives, glycols, etc. Coloring and flavoring agents may also be added to preparations, particularly those for oral administration. Solutions can be prepared using water or physiologically compatible organic solvents such as ethanol, 1,2-propylene glycol, polyglycols, dimethyl sulfoxide, fatty alcohols, triglycerides, partial esters of glycerine and the like. Parenteral compositions may be used for intravenous, intraarterial, intrarnuscular, intraperitoneal, intracutaneous or subcutaneous delivery. These preparations can be made using conventional techniques and may include sterile isotonic saline, water, 1,3-butanediol, ethanol, 1,2-propylene glycol, polyglycols nixed with water, Ringers' solution, etc.

Inhibitors and inducers of cell contraction can also be used in conjunction with matrices employed as implants to facilitate tissue healing and as scaffolds to be seeded with cells in vitro for subsequent implantation. In these cases, the inhibitors and inducers can be adsorbed by the matrix and, in some cases, chemically coupled to the matrix.

Advantages of Treatment Methods

The ability to control cell contraction has not been widely exploited as a therapeutic strategy. Thus, the methods discussed herein may serve to complement already established procedures. Because the expression and action of alpha-smooth muscle actin has been found to be responsible for the contraction of many different cell types and because contraction is important to many diverse biological processes, a single set of inhibitory or inducing agents may contribute to several treatment regimens.

EXAMPLES

Many types of injuries to the meniscus of the knee joint result in defects that do not heal, leading to pain and dysfunction. Several types of porous absorbable matrices may be used alone or seeded with cultured cells to facilitate regeneration of this tissue. The objective of the present study was to evaluate the in vitro contractile behavior of meniscal cells seeded in type I and type II collagen matrices.

In many connective tissues, fibroblasts that have assumed a contractile phenotype (myofibroblasts) have been found to play an important role in healing and in pathological conditions. This phenotype, if expressed in meniscal cells, may affect their behavior in cells seeded matrices developed for tissue engineering. In the present study, the presence of a contractile actin isoform, alpha-smooth muscle (alpha-SM actin), was assessed by immunohistochemistry in normal calf meniscal tissue and in meniscal cells in 2- and 3-dimensional culture.

Calf meniscus cells were seeded in type I and type II collagen-glycosaminoglycan (GAG) matrices. The diameter of the matrices was measured every two-three days. Immunohistochemical staining of the 2-dimensional cultures for alpha-SM actin was performed after 1, 3, and 7 days, and of the seeded matrices at 1, 7, 14, and 21 days. Transmission electron microscopy (TEM) was performed on selected samples.

After three weeks, the seeded type I matrices displayed a significant shrinkage of almost 50%, whereas the type II matrix and both types of unseeded controls showed almost no contraction over the same time period. Positive staining for the alpha-SM actin phenotype was seen in 10% of the cells of the normal tissue, but was present in all cells seeded in monolayer and in both types of matrices. TEM of representative cell-seeded matrices showed microfilaments approximately 7 nm bic, consistent with the myofibroblast phenotype. To our knowledge, there are no other reports of alpha-SM actin-containing cells in the intact knee meniscus. The finding that, under certain conditions, meniscal cells can express the myofibroblast phenotype suggests a role in meniscal healing and the tissue response to implants to facilitate tissue regeneration.

All references cited are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of treating a patient for damaged musculoskeletal tissue damaged epithelial tissue, comprising:
   a) administering an alpha-smooth muscle actin (SMA) inhibitor at the site of said damaged musculoskeletal tissue or damaged epithelial tissue, said SMA inhibitor being administered at a dosage and for a duration sufficient to promote the reattachment of torn ends of said tissue or the attachment of said tissue to bone; and after said reattachment of said torn ends of said tissue or attachment of said tissue to said bone,
   b) administering an SMA inducer at the site of said damaged musculoskeletal tissue or damaged epithelial tissue, said inducer being administered at a dosage and for a duration sufficient to promote the contraction of the reattached or attached tissue of step a).

2. The method of claim 1, wherein said damaged musculoskeletal tissue or epithelial tissue is a damaged ligament.

3. The method of either claim 1 or claim 2, wherein said SMA inducer is transforming growth factor-beta (TGF-beta).

4. The method of either claim 1 or claim 2, wherein said SMA inhibitor is selected from the group consisting of platelet derived growth factor (PDGF) and an interferon.

5. The method of claim 4, wherein said SMA inducer is TGF-beta.

6. The method of claim 1, wherein said method is applied to the treatment of damaged musculoskeletal tissue.

7. The method of claim 6, wherein said SMA inhibitor is administered for a period of 1 to 10 weeks.

8. The method of claim 6, wherein SMA inducer is TGF-beta.

9. The method of claim 8, wherein said TGF-beta is injected at a concentration of between 100 ng/ml and 500 µg/ml.

10. The method of any one of claims 6–9, wherein said SMA inhibitor is PDGF or an interferon.

11. The method of claim 10, wherein the site of tissue damage is a patient's knee.

12. The method of claim 11, wherein said damaged musculoskeletal tissue is a torn ligament.

13. The method of any one of claims 6–9 wherein the site of tissue damage is a patient's knee.

14. The method of claim 13, wherein said damaged musculoskeletal tissue is a torn ligament.

15. The method of claim 1, wherein said method is applied to the treatment of damaged epithelial tissue.

16. The method of claim 15, wherein said SMA inhibitor is administered for a period of 1 to 10 weeks.

17. The method of claim 15, wherein SMA inducer is TGF-beta.

18. The method of claim 17, wherein said TGF-beta is injected at a concentration of between 100 ng/ml and 500 µg/ml.

19. The method of any one of claims 15–18, wherein said SMA inhibitor is PDGF or an interferon.

* * * * *